United States Patent [19]

Kume et al.

[11] Patent Number: 5,158,600
[45] Date of Patent: Oct. 27, 1992

[54] HERBICIDAL 3-HYDROXY-2-CYCLOHEXEN-1-ONES

[75] Inventors: Toyohiko Kume, Hino; Toshio Goto, Kokubunji; Atsumi Kamochi, Oyama; Hidenori Hayakawa, Oyama; Tadao Asami, Oyama; Akihiko Yanagi, Oyama, all of Japan

[73] Assignee: Nihon Tokushu Noyaku Seizo K.K., Tokyo, Japan

[21] Appl. No.: 695,873

[22] Filed: May 6, 1991

[30] Foreign Application Priority Data

May 16, 1990 [JP] Japan ................. 2-124224

[51] Int. Cl.⁵ ............... A01N 31/02; C07C 251/36
[52] U.S. Cl. ........................... 71/98; 564/250; 564/300; 71/103
[58] Field of Search ............. 564/256, 300; 71/98, 71/103

[56] References Cited

U.S. PATENT DOCUMENTS

| | | | |
|---|---|---|---|
| 4,249,937 | 2/1981 | Iwataki et al. | 71/97 |
| 4,460,402 | 7/1984 | Holm | 71/98 |
| 4,728,357 | 3/1988 | Becker et al. | 71/98 |
| 4,950,322 | 8/1990 | Arai et al. | 71/98 |
| 4,981,971 | 1/1991 | Arai et al. | 546/296 |

FOREIGN PATENT DOCUMENTS

| | | |
|---|---|---|
| 0254514 | 1/1988 | European Pat. Off. |
| 0262265 | 4/1988 | European Pat. Off. |
| 2391999 | 12/1978 | France |
| 64-13066 | 1/1989 | Japan |

OTHER PUBLICATIONS

Chemical Abstracts, vol. 111, No. 17, Oct. 23, 1989, Columbus, Ohio, US: & JP-A-0113066 (Sumitomo Chemical Co. Ltd) Jan. 17, 1989, Cat. D, p. 676, Left-hand column, ref. No. 153359J.

*Primary Examiner*—Richard L. Raymond
*Assistant Examiner*—Brian M. Burn
*Attorney, Agent, or Firm*—Sprung Horn Kramer & Woods

[57] ABSTRACT

Herbicidal 3-hydroxy-2-cyclohexen-1-ones of the formula

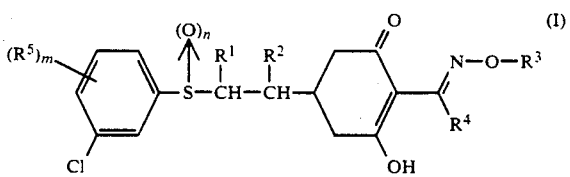

wherein
$R^1$ and $R^2$ each is hydrogen or methyl,
$R^3$ is $C_{1-4}$ alkyl, cyclopropylmethyl, $C_{3-4}$ alkenyl which may be substituted by one to three halogen atoms or $C_{3-4}$ alkynyl,
$R^4$ is $C_{1-4}$ alkyl,
$R^5$ each independently is halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio or cyano,
n is 0, 1 or 2, and
m is 0, 1 or 2.

13 Claims, No Drawings

HERBICIDAL 3-HYDROXY-2-CYCLOHEXEN-1-ONES

The present invention relates to novel 3-hydroxy-2-cyclohexen-1-ones, to processes for their preparation and to their use as herbicides.

It has already been disclosed that a certain group of cyclohexane derivatives has herbicidal activities. (see Japanese Patent Laid-open Nos. 115,349/1979, 146,856/1988 and 13066/1989)

There have now been found novel 3-hydroxy-2-cyclohexen-1-ones of the formula (I)

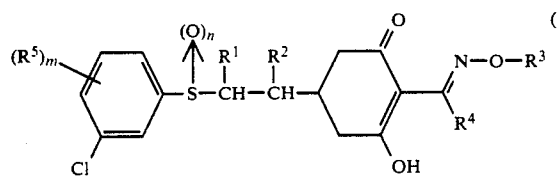

wherein
$R^1$ and $R^2$ each is hydrogen or methyl,
$R^3$ is $C_{1-4}$ alkyl, cyclopropylmethyl,
$C_{3-4}$ alkenyl which may be substituted by one to three halogen atoms or $C_{3-4}$ alkynyl,
$R^4$ is $C_{1-4}$ alkyl,
$R^5$ each independently is halogen, $C_{1-4}$ alkyl, $C_{1-4}$ haloalkyl $C_{1-4}$ alkoxy, $C_{1-4}$ haloalkoxy, $C_{1-4}$ alkylthio, $C_{1-4}$ haloalkylthio or cyano,
n is 0, 1 or 2, and
m is 0, 1 or 2.

The compounds of the formula (I) can be obtained by a process in which,
a) where n is 0;
compounds of the formula (II)

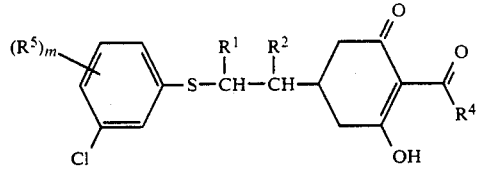

wherein $R^1$, $R^2$, $R^4$, $R^5$ and m have the same meanings as mentioned above, are reacted with compounds of the formula (III)

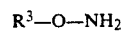

R³—O—NH₂ (III)

wherein $R^3$ has the same meaning as mentioned above, or a salt of the compounds of the formula (III), in the presence of inert solvents, and if appropriate, in the presence of an acid binder, and
b) where n is 1 or 2;
compounds of the formula (Ia)

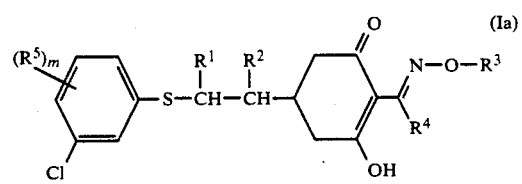

wherein $R^1$, $R^2$, $R^3$, $R^4$, $R^5$ and m have the same meanings as mentioned before, are reacted with an oxidizing agent in the presence of inert solvents.

The novel 3-hydroxy-2-cyclohexen-1-ones exhibit powerful herbicidal properties.

Surprisingly, the compounds of the formula (I) according to the invention exhibit not only a substantially greater herbicidal action than those known from the aforesaid prior art, but also favorable compatibility with crops.

In the formula (I) of the compounds according to the present invention, preferably $R^1$ and $R^2$ each represent hydrogen or methyl,
$R^3$ represents $C_{1-4}$ alkyl or $C_{3-4}$ alkenyl that may be substituted by one to three halogen atoms,
$R^4$ represents $C_{1-3}$ alkyl,
$R^5$ represents chlorine, fluorine or trifluoromethyl,
n is 0, 1 or 2, and
m is 0, 1 or 2 wherein when m is 2, $R^5$ may be the same or different.

Further, in the formula (I), most preferably,
$R^1$ and $R^2$ each represent hydrogen,
$R^3$ represents ethyl or allyl, by chlorine,
$R^4$ represents methyl or ethyl,
$R^5$ represents chlorine, fluorine or trifluoromethyl,
n is 0, and
m is 0 or 1.

Specifically, the following compounds may be mentioned:

5-[2-(3,4-dichlorophenylthio)ethyl]-3-hydroxy-2-(1-ethoxyimino)propyl-2-cyclohexen-1-one;

5-[2-(3-chlorophenylthio)ethyl]-3-hydroxy-2-(1-ethoxyimino)propyl-2-cyclohexen-1-one;

5-[2-(3-chloro-4-fluorophenylthio)ethyl]-3-hydroxy-2-(1-ethoxyimino)propyl-2-cyclohexen-1-one;

5-{2-[3-chloro-4-(trifluoromethyl)phenylthio]ethyl}-3-hydroxy-2-(1-ethoxyimino)-ethyl-2-cyclohexen-1-one;

5-[2-(3-chloro-2-methylphenylthio)ethyl]-3-hydroxy-2-(1-allyloxyimino)propyl-2-cyclohexen-1-one;

5-[2-(3-chloro-4-fluorophenylthio)ethyl]-3-hydroxy-2-(1-allyloximino)propyl-2-cyclohexen-1-one;

5-[2-(2-methyl-3-chlorophenylthio)ethyl]-3-hydroxy-2-(1-ethoxyimino)propyl-2-cyclohexen-1-one.

If, for example, in the above process a), 5-[2-(3,4-dichlorophenylthio)ethyl]-3-hydroxy-2-propionyl-2-cyclohexen-1-one and O-methylhydroxylamine hydrochloride are used as the starting materials, the reaction can be represented as follows:

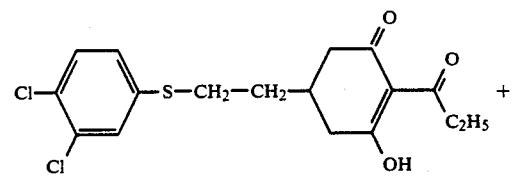

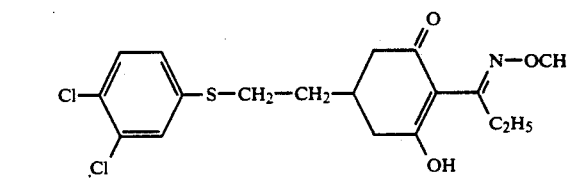

If, for example, in the above process b), 5-[2-(3,5-dichlorophenylthio)ethyl]-3-hydroxy-2-(1-ethoxyimino)propyl-2-cyclohexen-1-one and meta-chloro perbenzoic acid are used as the starting materials, for example, the reaction can be represented as follows:

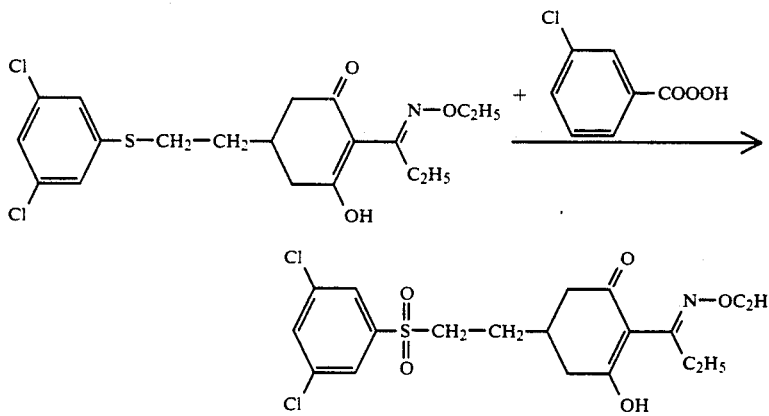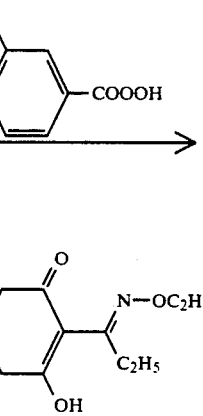

The compounds of the formula (II) include novel compounds that can be prepared by rearranging compounds of the formula (IV)

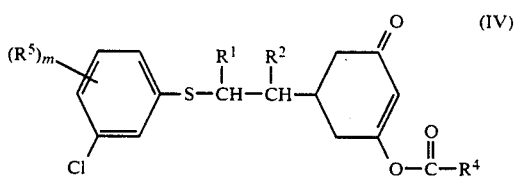

wherein $R^1$, $R^2$, $R^4$, $R^5$ and m have the same meanings as mentioned before.

The above compounds of the formula (IV) can be prepared by reacting compounds of the formula (V)

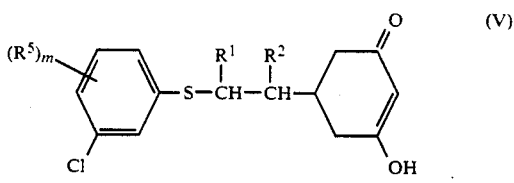

wherein $R^1$, $R^2$, $R^5$ and m have the same meanings as mentioned before, with compounds of the formula (VI)

wherein $R^4$ has the same meaning as mentioned before and Hal means a halogen atom.

The compounds of the formula (V) can be prepared by a process disclosed in Japanese Patent Laid-open No. 13066/1989.

The compounds of the formula (VI) are well known in organic chemistry and as an example, there may be mentioned propionyl chloride.

The compounds represented by the general formula (III) are well known in organic chemistry and, as examples, there may be mentioned the following O-methylhydroxylamine, O-ethylhydroxylamine and O-allylhydroxylamine, and hydrochlorides thereof.

In the above process b), the compounds of the formula (Ia) can be prepared by the above process a) and said compounds are a part of the compounds of formula (I).

As examples thereof, there may be mentioned:

5-[2-(3,4-dichlorophenylthio)ethyl]-3-hydroxy-2-(1-ethoxyimino)propyl-2-cyclohexen-1-one and
5-[2-(3-chloro-4-methylthiophenylthio)ethyl]-3-hydroxy-2-(1-ethoxyimino)propyl-2-cyclohexen-1-one.

As the oxidizing agent used in the above process b), use may be made, for example, of organic peroxides such as meta-chloroperbenzoic acid, hydrogen peroxide and the like.

In carrying out the process a) mentioned above, use may be made, as suitable diluent, of any inert solvent.

Examples of such diluents are water; aliphatic, cycloaliphatic and aromatic, optionally chlorinated, hydrocarbons such as hexane, cyclohexane, petroleum ether, ligroin, benzene, toluene, xylene, methylene chloride, chloroform, carbon tetrachloride, ethylene chloride, 1,2-dichloroethane, chlorobenzene, dichlorobenzene and the like; ethers such as diethyl ether, methyl ethyl ether, di-isopropyl ether, dibutyl ether, dioxane, tetrahydrofuran and the like; nitriles such as acetonitrile, propionitrile, acrylonitrile and the like; alcohols such as methanol, ethanol, iso-propanol, butanol, ethylene glycol, 2-methoxy ethanol and the like, esters such as ethyl acetate, amyl acetate and the like; acid amides such as dimethyl formamide, N,N-dimethylacetamide and the like and sulfones and sulfoxides such as dimethylsulfoxide, sulfolane and the like; and bases, for example, such as pyridine.

The above-mentioned process a) is carried out preferably in the presence of an acid binder and, as the acid binder, there may be mentioned, for example, the hydroxide, carbonate, bicarbonate and alcoholate of alkali metals, tertiary amines such as, for example, triethylamine, tributylamine, 1,1,4,4-tetramethylethylenediamine, N,N-dimethylaniline, N,N-diethylaniline, pyridine, 4-dimethylamino pyridine (DMAP), 1,4-diazabicyclo[2,2,2]octane (DABCO), and 1,8-diazabicyclo[5,4,-0]undec-7-ene (DBU).

In the above-mentioned process a), the reaction temperature can be varied within a substantially wide range. In general, the reaction is carried out at a temperature of from about 0° C. to 100° C., preferably at room temperature.

Further, the reaction is carried out under normal pressure, although it is also possible to employ a higher or reduced pressure.

When the above-mentioned process a) according to the present invention is carried out, use is made, for example, of about once or twice moles of the compounds of the formula (III) per mole of the compounds of the formula (II) in the presence of 1.0 to 2.0 triethylamine dissolved in an inert solvent such as methanol, for example, to obtain the desired compound.

When use is made, in carrying out the process b) mentioned above, of organic peroxides as oxidizing agent, the following solvents may be used as suitable diluents:

aliphatic, cycloaliphatic and aromatic, optionally chlorinated, hydrocarbons such as hexane, cyclohexane, petroleum ether, ligroin, benzene, toluene, xylene, methylene chloride, chloroform, carbon tetrachloride, ethylene chloride, 1,2-dichloroethane, chlorobenzene, dichlorobenzene and the like; alcohols such as methanol, ethanol, iso-propanol, butanol, ethylene glycol, 2-methoxyethanol and the like; esters such as ethyl acetate, amyl acetate; and acid amides such as dimethyl formamide, dimethyl acetamide and the like.

When use is made, in carrying out the above-mentioned process b), of hydrogen peroxide as oxidizing agent, the following solvents may be used as suitable solvents:

water that may be basic, neutral or acidic; alcohols such as, for example, methanol, ethanol, iso-propanol, butanol, ethyleneglycol, 2-methoxyethanol; carboxylic acids such as acetic acid for example.

In the above-mentioned process b), the reaction temperature can be varied within a substantially wide range. When n is 1 in formula (I), the reaction is carried out, in general, at a temperature of from about 0° C. to about 25° C., preferably from about 0° C. to about 10° C. When n is 2, the temperature may be from about 50° C. to about 100° C., preferably from about 80° C. to about 100° C.

The reaction is preferably carried out under normal pressure, although it is also possible to employ a higher or reduced pressure.

When the above-mentioned process b) according to the present invention is carried out, use is made, for example, of about 1.0 to 2.4 moles of meta-chloroperbenzoic acid per mole of the compounds of the formula (Ia) in the presence of an inert solvent such as, for example, methanol to obtain the desired compound.

The active compounds according to the invention can be used as defoliants, desiccants, agents for destroying broad-leaved plants and, especially, as weedkillers. By weed, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Possible components for the mixtures are known herbicides, such as, for example, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beets and 4-amino-6-(1,1-dimethylethyl)-3-methylthio-1,2,4-triazin-5(4H)-one for combating weeds in soy beans. Surprisingly, some mixtures also show a synergistic action.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between about 0.04 and 4 kg of active compound per hectare of soil surface, preferably between about 0.05 and 2 kg per ha.

The preparation and use of the active compounds according to the invention can be seen from the following examples.

PREPARATIVE EXAMPLES

EXAMPLE 1

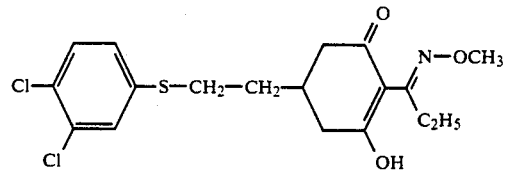

To a solution of 5-[2-(3,4-dichlorophenylthio)ethyl]-3-hydroxy-2-propionyl-2-cyclohexen-1-one (0.75 g) and triethylamine (0.4 g) dissolved in methanol (15 ml) was added O-methylhydroxylamine hydrochloride (0.02 g) and the mixture solution was agitated at room temperature for 12 hours. After the reaction of the mixture solution had been completed, the solvent was distilled off, followed by addition of dilute hydrochloric acid thereto. The reaction product was extracted with ethyl acetate three times and, after drying over anhydrous sodium sulfate, was freed from the solvent by evaporation under reduced pressure. The thus obtained oily residue was purified through silicagel column chromatography (hexane:ethylacetate=2:1) to give 5-[2-(3,4-dichlorophenylthio)ethyl]-3-hydroxy-2-(1-methoxyimino)propyl-2-cyclohexen-1-one (0.62 g). $n_D^{20}$ 1.5909.

Together with the compound obtained in Example 1, Table 1 which follows sets forth compounds which can be obtained by the same method as in Example 1:

TABLE 1

| Comp. No. | $R^1$ | $R^2$ | $R^3$ | $R^4$ | $(R^5)_m$ | n | |
|---|---|---|---|---|---|---|---|
| 1 | H | H | $CH_2CH_3$ | $CH_3$ | — | 0 | |
| 2 | H | H | $CH_2CH_2CH_3$ | $CH_3$ | — | 0 | $n_D^{20}$ 1.5904 |
| 3 | H | H | $CH_2CH=CH_2$ | $CH_3$ | — | 0 | $n_D^{20}$ 1.5934 |
| 4 | H | H | $CH_2CH=CHCl$ | $CH_3$ | — | 0 | $n_D^{20}$ 1.5883 |
| 5 | H | H | $CH_3$ | $C_2H_5$ | — | 0 | $n_D^{20}$ 1.5989 |
| 6 | H | H | $CH_2CH_3$ | $C_2H_5$ | — | 0 | $n_D^{20}$ 1.5967 |
| 7 | H | H | $CH_2CH_2CH_3$ | $C_2H_5$ | — | 0 | $n_D^{20}$ 1.5802 |
| 8 | H | H | $CH_2CH=CH_2$ | $C_2H_5$ | — | 0 | $n_D^{20}$ 1.5901 |
| 9 | H | H | $CH_2CH=CHCl$ | $C_2H_5$ | — | 0 | $n_D^{20}$ 1.5807 |

TABLE 1-continued $$\text{(R}^5)_m\text{-C}_6\text{H}_3\text{(Cl)-S(O)}_n\text{-CH(R}^1\text{)-CH(R}^2\text{)-[cyclohexenone with =N-O-R}^3\text{, R}^4\text{, OH, =O]}$$

| Comp. No. | $R^1$ | $R^2$ | $R^3$ | $R^4$ | $(R^5)_m$ | n | |
|---|---|---|---|---|---|---|---|
| 10 | H | H | $CH_3$ | $CH_2CH_2CH_3$ | — | 0 | |
| 11 | H | H | $CH_2CH_3$ | $CH_2CH_2CH_3$ | — | 0 | $n_D^{20}$ 1.5792 |
| 12 | H | H | $CH_2CH_2CH_3$ | $CH_2CH_2CH_3$ | — | 0 | |
| 13 | H | H | $CH_2CH=CH_2$ | $CH_2CH_2CH_3$ | — | 0 | $n_D^{20}$ 1.5383 |
| 14 | H | H | $CH_2CH=CHCl$ | $CH_2CH_2CH_3$ | — | 0 | $n_D^{20}$ 1.5685 |
| 15 | H | H | $CH_2C\equiv CH$ | $CH_2CH_2CH_3$ | — | 0 | |
| 16 | H | $CH_3$ | $CH_2CH_3$ | $CH_3$ | 5-Cl | 0 | |
| 17 | H | $CH_3$ | $CH_2CH_2CH_3$ | $CH_3$ | 5-Cl | 0 | |
| 18 | H | $CH_3$ | $CH_2CH=CH_2$ | $CH_3$ | 5-Cl | 0 | |
| 19 | H | $CH_3$ | $CH_2CH=CHCl$ | $CH_3$ | 5-Cl | 0 | |
| 20 | H | $CH_3$ | $CH_3$ | $C_2H_5$ | 5-Cl | 0 | |
| 21 | H | $CH_3$ | $CH_2CH_3$ | $C_2H_5$ | 5-Cl | 0 | $n_D^{20}$ 1.5850 |
| 22 | H | $CH_3$ | $CH_2CH_2CH_3$ | $C_2H_5$ | 5-Cl | 0 | $n_D^{20}$ 1.5951 |
| 23 | H | $CH_3$ | $CH_2CH=CH_2$ | $C_2H_5$ | 5-Cl | 0 | |
| 24 | H | $CH_3$ | $CH_2CH_2CH_3$ | $CH_2CH_2CH_3$ | 5-Cl | 0 | |
| 25 | H | $CH_3$ | $CH_2C\equiv CH$ | $CH_2CH_2CH_3$ | 5-Cl | 0 | |
| 26 | H | H | $CH_3$ | $C_2H_5$ | 6-Cl | 0 | $n_D^{20}$ 1.5576 |
| 27 | H | H | $CH_2CH_3$ | $C_2H_5$ | 6-Cl | 0 | $n_D^{20}$ 1.5736 |
| 28 | H | H | $CH_2CH_2CH_3$ | $C_2H_5$ | 6-Cl | 0 | |
| 29 | H | H | $CH_2CH=CH_2$ | $C_2H_5$ | 6-Cl | 0 | |
| 30 | H | H | $CH_2CH=CHCl$ | $C_2H_5$ | 6-Cl | 0 | |
| 31 | H | H | $CH_2C\equiv CH$ | $C_2H_5$ | 6-Cl | 0 | |
| 32 | H | H | $CH_2CH_3$ | $CH_3$ | 5-Cl | 0 | Oily |
| 33 | H | H | $CH_2CH_2CH_3$ | $CH_3$ | 5-Cl | 0 | $n_D^{20}$ 1.5911 |
| 34 | H | H | $CH_2CH=CH_2$ | $CH_3$ | 5-Cl | 0 | $n_D^{30}$ 1.5941 |
| 35 | H | H | $CH_2CH=CHCl$ | $CH_3$ | 5-Cl | 0 | |
| 36 | H | H | $CH_2C\equiv CH$ | $CH_3$ | 5-Cl | 0 | |
| 37 | H | H | $CH_3$ | $C_2H_5$ | 5-Cl | 0 | $n_D^{20}$ 1.6049 |
| 38 | H | H | $CH_2CH_3$ | $C_2H_5$ | 5-Cl | 0 | |
| 39 | H | H | $CH_2CH_2CH_3$ | $C_2H_5$ | 5-Cl | 0 | $n_D^{20}$ 1.5806 |
| 40 | H | H | $CH_2CH=CH_2$ | $C_2H_5$ | 5-Cl | 0 | $n_D^{20}$ 1.5923 |
| 41 | H | H | $CH_2CH=CHCl$ | $C_2H_5$ | 5-Cl | 0 | |
| 42 | H | H | $CH_2C\equiv CH$ | $C_2H_5$ | 5-Cl | 0 | |
| 43 | H | H | $CH_3$ | $CH_2CH_2CH_3$ | 5-Cl | 0 | Oily |
| 44 | H | H | $CH_2CH_3$ | $CH_2CH_2CH_3$ | 5-Cl | 0 | Oily |
| 45 | H | H | $CH_2CH_2CH_3$ | $CH_2CH_2CH_3$ | 5-Cl | 0 | $n_D^{20}$ 1.5803 |
| 46 | H | H | $CH_2CH=CH_2$ | $CH_2CH_2CH_3$ | 5-Cl | 0 | Oily |
| 47 | H | H | $CH_2CH=CHCl$ | $CH_2CH_2CH_3$ | 5-Cl | 0 | |
| 48 | H | H | $CH_2C\equiv CH$ | $CH_2CH_2CH_3$ | 5-Cl | 0 | |
| 49 | $CH_3$ | H | $CH_2CH_3$ | $CH_3$ | 5-Cl | 0 | |
| 50 | $CH_3$ | H | $CH_2CH_2CH_3$ | $CH_3$ | 5-Cl | 0 | |
| 51 | $CH_3$ | H | $CH_2CH=CH_2$ | $CH_2CH_2CH_3$ | 5-Cl | 0 | $n_D^{20}$ 1.5799 |
| 52 | $CH_3$ | H | $CH_2CH_3$ | $CH_2CH_2CH_3$ | 5-Cl | 0 | $n_D^{20}$ 1.5850 |
| 53 | $CH_3$ | H | $CH_3$ | $CH_2CH_2CH_3$ | 5-Cl | 0 | $n_D^{20}$ 1.5945 |
| 54 | $CH_3$ | H | $CH_3$ | $C_2H_5$ | 5-Cl | 0 | $n_D^{20}$ 1.5984 |
| 55 | $CH_3$ | H | $CH_2CH_3$ | $C_2H_5$ | 5-Cl | 0 | $n_D^{20}$ 1.5845 |
| 56 | $CH_3$ | H | $CH_2CH_2CH_3$ | $C_2H_5$ | 5-Cl | 0 | $n_D^{20}$ 1.5776 |
| 57 | $CH_3$ | H | $CH_2CH=CH_2$ | $C_2H_5$ | 5-Cl | 0 | $n_D^{20}$ 1.5934 |
| 58 | $CH_3$ | H | $CH_2CH_2CH_3$ | $CH_2CH_2CH_3$ | 5-Cl | 0 | $n_D^{20}$ 1.5713 |
| 59 | H | H | $CH_2CH_3$ | $C_2H_5$ | — | 1 | $n_D^{20}$ 1.5470 |
| 60 | H | H | $CH_2CH_3$ | $CH_3$ | 5-Cl | 1 | |
| 61 | H | H | $CH_2CH=CH_2$ | $CH_3$ | 5-Cl | 1 | |
| 62 | H | H | $CH_2CH_3$ | $C_2H_5$ | 5-Cl | 1 | $n_D^{20}$ 1.5630 |
| 63 | H | H | $CH_3$ | $C_2H_5$ | — | 2 | |
| 64 | H | H | $CH_2CH_3$ | $C_2H_5$ | — | 2 | |
| 65 | H | H | $CH_2CH=CH_2$ | $C_2H_5$ | — | 2 | |
| 66 | H | H | $CH_2CH_3$ | $CH_3$ | 5-Cl | 2 | |
| 67 | H | H | $CH_2CH_3$ | $CH_3$ | 2-Cl | 0 | mp 60.5–65° C. |
| 68 | H | H | $CH_2CH_2CH_3$ | $CH_3$ | 2-Cl | 0 | |
| 69 | H | H | $CH_2CH=CH_2$ | $CH_3$ | 2-Cl | 0 | mp 60–62° C. |
| 70 | H | H | $CH_2CH=CHCl$ | $CH_3$ | 2-Cl | 0 | |
| 71 | H | H | $CH_3$ | $CH_3$ | 2-Cl | 0 | mp 95.5–100° C. |
| 72 | H | H | $CH_3$ | $C_2H_5$ | 2-Cl | 0 | mp 55–62° C. |
| 73 | H | H | $CH_2CH_3$ | $C_2H_5$ | 2-Cl | 0 | $n_D^{20}$ 1.5983 |
| 74 | H | H | $CH_2CH_2CH_3$ | $C_2H_5$ | 2-Cl | 0 | |
| 75 | H | H | $CH_2CH=CH_2$ | $C_2H_5$ | 2-Cl | 0 | mp 49–56.5° C. |
| 76 | H | H | $CH_2CH=CHCl$ | $C_2H_5$ | 2-Cl | 0 | |
| 77 | H | H | $CH_2C\equiv CH$ | $C_2H_5$ | 2-Cl | 0 | |
| 78 | H | H | $CH_3$ | $C_2H_5$ | 4-Cl | 0 | $n_D^{20}$ 1.5909 |
| 79 | H | H | $CH_2CH_3$ | $C_2H_5$ | 4-Cl | 0 | $n_D^{20}$ 1.5917 |
| 80 | H | H | $CH_2CH=CH_2$ | $C_2H_5$ | 4-Cl | 0 | $n_D^{20}$ 1.5987 |
| 81 | H | H | $CH_2CH=CHCl$ | $C_2H_5$ | 4-Cl | 0 | $n_D^{20}$ 1.6002 |

TABLE 1-continued

| Comp. N | R¹ | R² | R³ | R⁴ | (R⁵)ₘ | n | |
|---|---|---|---|---|---|---|---|
| 82 | H | H | CH₃ | CH₃ | 4-Cl | 0 | $n_D^{20}$ 1.6112 |
| 83 | H | H | CH₂CH=CH₂ | CH₃ | 4-Cl | 0 | $n_D^{20}$ 1.5960 |
| 84 | H | H | CH₂CH₃ | CH₃ | 4-Cl | 0 | $n_D^{20}$ 1.5855 |
| 85 | H | H | CH₂CH₃ | CH₃ | 4-F | 0 | $n_D^{20}$ 1.5793 |
| 86 | H | H | CH₂CH=CH₂ | CH₃ | 4-F | 0 | $n_D^{20}$ 1.5751 |
| 87 | H | H | CH₂CH=CHCl | CH₃ | 4-F | 0 | |
| 88 | H | H | CH₃ | C₂H₅ | 4-F | 0 | $n_D^{20}$ 1.5603 |
| 89 | H | H | CH₂CH₃ | C₂H₅ | 4-F | 0 | $n_D^{20}$ 1.5359 |
| 90 | H | H | CH₂CH=CHCl | C₂H₅ | 4-F | 0 | $n_D^{20}$ 1.5810 |
| 91 | H | H | CH₂CH₃ | CH₃ | 2-F | 0 | $n_D^{20}$ 1.5852 |
| 92 | H | H | CH₂CH₂CH₃ | CH₃ | 2-F | 0 | |
| 93 | H | H | CH₂CH=CH₂ | CH₃ | 2-F | 0 | |
| 94 | H | H | CH₂CH=CHCl | CH₃ | 2-F | 0 | |
| 95 | H | H | CH₂C≡CH | CH₃ | 2-F | 0 | |
| 96 | H | H | CH₃ | C₂H₅ | 2-F | 0 | |
| 97 | H | H | CH₂CH₃ | C₂H₅ | 2-F | 0 | |
| 98 | H | H | CH₂CH=CH₂ | C₂H₅ | 2-F | 0 | |
| 99 | H | H | CH₂CH=CHCl | C₂H₅ | 2-F | 0 | |
| 100 | H | H | CH₃ | CH₂CH₂CH₃ | 2-F | 0 | |
| 101 | H | H | CH₂CH₃ | CH₂CH₂CH₃ | 2-F | 0 | |
| 102 | H | H | CH₂CH=CH₂ | CH₂CH₂CH₃ | 2-F | 0 | |
| 103 | H | H | CH₂CH=CHCl | CH₂CH₂CH₃ | 2-F | 0 | |
| 104 | H | H | CH₂CH₃ | CH₃ | 4-OCH₃ | 0 | $n_D^{20}$ 1.5872 |
| 105 | H | H | CH₂CH=CH₂ | CH₃ | 4-OCH₃ | 0 | $n_D^{20}$ 1.5902 |
| 106 | H | H | CH₂CH=CHCl | CH₃ | 4-OCH₃ | 0 | |
| 107 | H | H | CH₂C≡CH | CH₃ | 4-OCH₃ | 0 | |
| 108 | H | H | CH₃ | C₂H₅ | 4-OCH₃ | 0 | |
| 109 | H | H | CH₂CH₃ | C₂H₅ | 4-OCH₃ | 0 | $n_D^{20}$ 1.5818 |
| 110 | H | H | CH₂CH=CH₂ | C₂H₅ | 4-OCH₃ | 0 | $n_D^{20}$ 1.5841 |
| 111 | H | H | CH₂CH=CHCl | C₂H₅ | 4-OCH₃ | 0 | |
| 112 | H | H | CH₂CH₃ | CH₃ | 6-OCH₃ | 0 | $n_D^{20}$ 1.5879 |
| 113 | H | H | CH₃ | CH₂CH₃ | 6-OCH₃ | 0 | $n_D^{20}$ 1.5827 |
| 114 | H | H | CH₂CH₃ | CH₂CH₃ | 6-OCH₃ | 0 | $n_D^{20}$ 1.5842 |
| 115 | H | H | CH₂CH₃ | CH₂CH₂CH₃ | 6-OCH₃ | 0 | |
| 116 | H | H | CH₂CH=CH₂ | CH₃ | 4-OCHF₂ | 0 | |
| 117 | H | H | CH₂CH₃ | C₂H₅ | 4-OCHF₂ | 0 | |
| 118 | H | H | CH₂CH=CH₂ | CH₃ | 4-OCF₃ | 0 | |
| 119 | H | H | CH₃ | C₂H₅ | 4-OCF₃ | 0 | |
| 120 | H | H | CH₂CH₃ | C₂H₅ | 4-OCF₃ | 0 | |
| 121 | H | H | CH₂CH=CH₂ | CH₃ | 4-CF₃ | 0 | |
| 122 | H | H | CH₂CH₃ | CH₃ | 6-F | 0 | |
| 123 | H | H | CH₂CH₃ | C₂H₅ | 6-F | 0 | |
| 124 | H | H | CH₂CH₃ | CH₃ | 4-SCF₃ | 0 | |
| 125 | H | H | CH₂CH₃ | C₂H₅ | 4-SCF₃ | 0 | |
| 126 | H | H | CH₂CH=CH₂ | CH₃ | 2-OCH₃ | 0 | |
| 127 | H | H | CH₂CH=CH₂ | CH₃ | 2-OCHF₂ | 0 | |
| 128 | H | H | CH₂CH₃ | C₂H₅ | 2-OCHF₂ | 0 | |
| 129 | H | H | CH₂CH=CHCl | CH₃ | 2-OCF₃ | 0 | |
| 130 | H | H | CH₂CH=CH₂ | CH₃ | 2-CH₃ | 0 | Oily |
| 131 | H | H | CH₂CH₃ | C₂H₅ | 2-CH₃ | 0 | $n_D^{20}$ 1.5539 |
| 132 | H | H | CH₂CH₃ | CH₃ | 4-CH₃ | 0 | $n_D^{20}$ 1.5871 |
| 133 | H | H | CH₂CH=CH₂ | CH₃ | 4-CH₃ | 0 | $n_D^{20}$ 1.5880 |
| 134 | H | H | CH₂CH₃ | C₂H₅ | 4-CH₃ | 0 | $n_D^{20}$ 1.5614 |
| 135 | H | H | CH₂CH₃ | CH₃ | 6-CH₃ | 0 | |
| 136 | H | H | CH₂CH=CH₂ | CH₃ | 6-CH₃ | 0 | |
| 137 | H | H | CH₃ | C₂H₅ | 6-CH₃ | 0 | |
| 138 | H | H | CH₂CH₃ | C₂H₅ | 6-CH₃ | 0 | |
| 139 | H | H | CH₂CH₃ | CH₃ | 4-CN | 0 | |
| 140 | H | H | CH₂CH=CH₂ | CH₃ | 4-CN | 0 | |
| 141 | H | H | CH₂CH₃ | C₂H₅ | 4-CN | 0 | |
| 142 | H | H | CH₂CH₃ | CH₃ | 4-SCH₃ | 0 | |
| 143 | H | H | CH₂CH=CH₂ | CH₃ | 4-SCH₃ | 0 | |
| 144 | H | H | CH₃ | CH₃ | 4-SCH₃ | 0 | mp 69–73° C. |
| 145 | H | H | CH₃ | C₂H₅ | 4-SCH₃ | 0 | |
| 146 | H | H | CH₂CH₃ | C₂H₅ | 4-SCH₃ | 0 | mp 53–60° C. |
| 147 | H | H | CH₂CH₃ | CH₃ | 4,5-Cl₂ | 0 | |
| 148 | H | H | CH₂CH=CH₂ | CH₃ | 4,5-Cl₂ | 0 | |
| 149 | H | H | CH₂CH=CHCl | CH₃ | 4,5-Cl₂ | 0 | |
| 150 | H | H | CH₃ | C₂H₅ | 4,5-Cl₂ | 0 | |
| 151 | H | H | CH₂CH₃ | C₂H₅ | 4,5-Cl₂ | 0 | |
| 152 | H | H | CH₂CH₃ | CH₃ | 4-F, 5-Cl | 0 | $n_D^{20}$ 1.5878 |
| 153 | H | H | CH₂CH=CH₂ | CH₃ | 4-F, 5-Cl | 0 | mp 56.5–61° C. |

TABLE 1-continued

[Structure: (R⁵)ₘ-phenyl-S(O)ₙ-CH(R¹)-CH(R²)-cyclohexenone with N-O-R³, R⁴, OH, and Cl substituent]

| Comp. No. | R¹ | R² | R³ | R⁴ | (R⁵)ₘ | n | |
|---|---|---|---|---|---|---|---|
| 154 | H | H | $CH_3$ | $C_2H_5$ | 4-F, 5-Cl | 0 | $n_D^{20}$ 1.5299 |
| 155 | H | H | $CH_2CH_3$ | $C_2H_5$ | 4-F, 5-Cl | 0 | $n_D^{20}$ 1.5532 |
| 156 | H | H | $CH_2CH=CH_2$ | $C_2H_5$ | 4-F, 5-Cl | 0 | |
| 157 | H | H | $CH_2CH=CH_2$ | $CH_3$ | 2,4-$F_2$ | 0 | |
| 158 | H | H | $CH_2CH_3$ | $C_2H_5$ | 2,4-$F_2$ | 0 | |
| 159 | H | H | $CH_2CH_2CH_3$ | $CH_3$ | 4-F, 6-Cl | 0 | |
| 160 | H | H | $CH_2CH_3$ | $C_2H_5$ | 4-F, 6-Cl | 0 | |
| 161 | H | H | $CH_2CH_3$ | $CH_3$ | 4,6-$F_2$ | 0 | $n_D^{20}$ 1.5719 |
| 162 | H | H | | $CH_3$ | 4,6-$F_2$ | 0 | |
| 163 | H | H | $CH_2CH=CH_2$ | $CH_3$ | 4,6-$F_2$ | 0 | |
| 164 | H | H | $CH_3$ | $C_2H_5$ | 4,6-$F_2$ | 0 | $n_D^{20}$ 1.5726 |
| 165 | H | H | $CH_2CH_3$ | $C_2H_5$ | 4,6-$F_2$ | 0 | $n_D^{20}$ 1.5662 |
| 166 | H | H | $CH_2CH_2CH_3$ | $C_2H_5$ | 4,6-$F_2$ | 0 | |
| 167 | H | H | $CH_2CH=CH_2$ | $CH_3$ | 4,5-$F_2$ | 0 | |
| 168 | H | H | $CH_2CH_3$ | $C_2H_5$ | 4,5-$F_2$ | 0 | |
| 169 | H | H | $CH_2CH=CH_2$ | $C_2H_5$ | 5-$CF_3$, 6-Cl | 0 | |
| 170 | H | H | $CH_2CH=CH_2$ | $CH_3$ | 4-$OCH_3$, 5-$CF_3$ | 0 | |
| 171 | H | H | $CH_2CH_3$ | $CH_2CH_2CH_3$ | 4-$OCH_3$, 5-$CF_3$ | 0 | |
| 172 | H | H | $CH_2CH_3$ | $CH_3$ | 5-$CF_3$, 6-$OCH_3$ | 0 | |
| 173 | H | H | $CH_2CH_3$ | $C_2H_5$ | 2-$OCH_3$, 5-$CF_3$ | 0 | |
| 174 | H | H | $CH_2CH_3$ | $C_2H_5$ | 4-Cl, 5-$CF_3$ | 0 | |
| 175 | H | H | $CH_2CH_3$ | $CH_3$ | 4-$OCF_3$, 5-$CH_3$ | 0 | |
| 176 | H | H | $CH_2CH_3$ | $C_2H_5$ | 4-$OCF_3$, 5-$CH_3$ | 0 | |
| 177 | H | H | $CH_2CH_3$ | $CH_3$ | 2-$OCH_3$, 5-$CF_3$ | 0 | |
| 178 | H | H | $CH_2CH_3$ | $C_2H_5$ | 2-$OCH_3$, 5-$CF_3$ | 0 | |
| 179 | H | H | $CH_2$-cyclopropyl | $C_2H_5$ | — | 0 | |
| 180 | H | H | $CH_2CH_3$ | $CH_3$ | 2-$CH_3$ | 0 | mp 58–61° C. |
| 181 | H | H | $CH_3$ | $C_2H_5$ | 2-$CH_3$ | 0 | $n_D^{20}$ 1.5822° C. |
| 182 | H | H | $CH_3$ | $CH_3$ | 4-F, 5-Cl | 0 | mp 78–84° C. |
| 183 | H | H | —$C_2H_5$ | —$CH_3$ | 4-$CF_3$ | 0 | mp. 52–58° C. |
| 184 | H | H | —$C_2H_5$ | —$C_2H_5$ | 4-$CF_3$ | 0 | mp. 48–56° C. |
| 185 | H | H | —$C_2H_5$ | —$CH_3$ | 4-$OCF_3$ | 0 | |
| 186 | H | H | —$C_2H_5$ | —$CH_3$ | 4-$OCHF_2$ | 0 | |
| 187 | H | H | —$CH_2CH=CH_2$ | —$CH_3$ | 4-$SCF_3$ | 0 | |
| 188 | H | H | —$CH_2CH=CHCl$ | —$CH_3$ | 4-Cl | 0 | $n_D^{20}$ 1.5870 |
| 189 | H | H | —$CH_2CH=CHCl$ | —$C_2H_5$ | 4-Cl | 0 | $n_D^{20}$ 1.6002 |
| 190 | H | H | —$CH_2CH=CH_2$ | —$C_3H_7$ | 4-Cl | 0 | $n_D^{20}$ 1.5740 |
| 191 | H | H | —$CH_2CH=CHCl$ | —$C_3H_7$ | 4-Cl | 0 | $n_D^{20}$ 1.5886 |
| 192 | H | H | —$CH_2CH=CHCl$ | —$C_2H_5$ | 2-$CH_3$ | 0 | $n_D^{20}$ 1.5875 |

BACKGROUND EXAMPLES

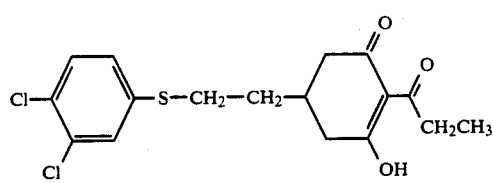

5-[2-(3,4-dichlorophenylthio)ethyl]-3-propionyloxy-2-cyclohexenone (1.63 g) and dimethylaminopyridine (0.45 g) were dissolved in acetonitrile (20 ml), followed by one-hour heat-refluxing. After the completion of the reaction, the reaction product was poured into diluted hydrochloric acid, followed by extraction with ethyl acetate three times. The organic phase was dried over anhydrous sodium sulfate and the solvent was removed by evaporation under reduced pressure and then the residue was purified through silicagel column chromatography (hexane:ethylacetate=85:15) to give 5-[2-(3,4-dichlorophenylthio)ethyl]-3-hydroxy-2-propionyl-2-cyclohexenone (1.44 g).

BIOTEST EXAMPLES

Comparative compounds:

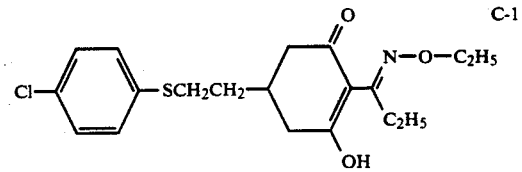

(Active compound disclosed by Japanese Patent Laid-open No. 115349/1979)

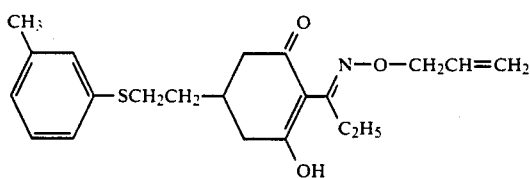

(Active compound disclosed by Japanese Patent Laid-open No. 115349/1979)

Example 2

Herbicidal test by foliage application on upland field weeds (I)

Formulation of Active Compounds

Carrier: 5 parts by weight of acetone
Emulsifier: 1 part by weight of benzyloxy polyglycol ether To produce a suitable preparation of active compound, 1 part by weight of each of the active compounds according to the present invention was mixed with the stated amount of carrier and with the stated amount of emulsifier, and the resulting emulsifiable concentrate was then diluted with water to the desired concentrations.

Test Procedures

In a greenhouse, a number of test pots each having an area of 1000 cm² were charged with soil taken from a cultivated field. Onto the soil surfaces in the respective test pots were sown and grown the seeds of barnyard grass (*Echinochloa crus-galli*), fingergrass (*Digitaria adscendens*), goose grass (*Eleusine indica*), green foxtail (*Setaria viridis*), oat (*Avena fatua L.*) and dent foxtail (*Alopeculus aequalis*), respectively. When the respective weeds had grown to heights in the range of from 3 to 10 cm in the test pots, predetermined dosages of the active compound formulation mentioned above were uniformly sprayed onto the foliage of the test weeds in the respective test pots.

Four weeks after the application of the active compound formulations, the degree of damage to the weeds and the degree of the phytotoxicity on the crop were determined based on the following assessment rate:

| Assessment rate of herbicidal effect | |
|---|---|
| 10: Herbicidal effect versus non-treated soil surface | 100% (completely killed) |
| 9: Herbicidal effect versus non-treated soil surface | 90% to less than 100% |
| 8: Herbicidal effect versus non-treated soil surface | from 80% to less than 90% |
| 7: Herbicidal effect versus non-treated soil surface | from 70% to less than 80% |
| 6: Herbicidal effect versus non-treated soil surface | from 60% to less than 70% |
| 5: Herbicidal effect versus non-treated soil surface | from 50% to less than 60% |
| 4: Herbicidal effect versus non-treated soil surface | from 40% to less then 50% |
| 3: Herbicidal effect versus non-treated soil surface | from 30% to less than 40% |
| 2: Herbicidal effect versus non-treated soil surface | from 20% to less than 30% |
| 1: Herbicidal effect versus non-treated soil surface | from 10% to less than 20% |
| 0: Herbicidal effect versus non-treated soil surface | less than 10% (no herbicidal effect) |
| Assessment rate of phytotoxicity | |
| 10: Herbicidal effect versus non-treated soil surface | 100% (completely killed fatal damage) |
| 9: Herbicidal effect versus non-treated soil surface | 90% to less than 100% |
| 8: Herbicidal effect versus non-treated soil surface | from 80% to less than 90% |
| 7: Herbicidal effect versus non-treated soil surface | from 70% to less than 80% |
| 6: Herbicidal effect versus non-treated soil surface | from 60% to less than 70% |
| 5: Herbicidal effect versus non-treated soil surface | from 50% to less than 60% |
| 4: Herbicidal effect versus non-treated soil surface | from 40% to less than 50% |
| 3: Herbicidal effect versus non-treated soil surface | from 30% to less than 40% |
| 2: Herbicidal effect versus non-treated soil surface | from 20% to less than 30% |
| 1: Herbicidal effect versus non-treated soil surface | from 10% to less than 20% |
| 0: Herbicidal effect versus non-treated soil surface | less than 10% (no phytotoxicity) |

The test results are shown in Table 2.

TABLE 2

| Active compound No. | Dosage of active compound g/ha | Barnyard grass | Finger grass | Goose grass | Green foxtail | Oat | Dent foxtail |
|---|---|---|---|---|---|---|---|
| 2 | 500 | 10 | 10 | 10 | 10 | 10 | — |
| 3 | 500 | 10 | 10 | 10 | 10 | 10 | — |
| 5 | 500 | 10 | 10 | 10 | 10 | 10 | 10 |
| 21 | 500 | 10 | 9 | 9 | 9 | 10 | 10 |
| 37 | 500 | 10 | 10 | 10 | 10 | 10 | 10 |
| 67 | 500 | 10 | 10 | 10 | 10 | 9 | — |
| 69 | 500 | 10 | 10 | 10 | 10 | 9 | — |
| 83 | 500 | 10 | 10 | 10 | 10 | 10 | 10 |
| 89 | 500 | 10 | 10 | 10 | 10 | 10 | — |
| 114 | 500 | 10 | 8 | 9 | 7 | 9 | — |
| 131 | 500 | 10 | 10 | 10 | 10 | 10 | — |

Example 3

Post-emergence foliage treatment on upland field weeds

In a greenhouse, a number of test pots each having an area of 2000 cm² were charged with soil taken from a cultivated field. Seeds of soy bean were sown onto the soil surfaces in the respective test pots. Each of the thus sown soil surfaces was covered with a soil layer to a height of 1 cm. Into the soil of the respective soil layers in the respective test pots had beforehand been mixed the seeds of barnyard grass, finger grass, goose grass, green foxtail, causeway grass (*Poa annua*) and Bermuda grass (*Cynodon dactylon*), respectively.

Ten days after the seed-sowing and soil-covering when the weeds entered the second leaf stage on average while the soy beans entered the early leafing stage of true leaves, predetermined dosages of the active compound formulations prepared as in Example 2 mentioned above were uniformly sprayed onto the foliage of the test plants in the respective test pots.

Three weeks after the spraying of the active compound formulations, the degree of the herbicidal effect on the weeds and the degree of the phytotoxicity on the crop were determined in a similar manner as in Example 2, the results of which are shown in Table 3:

TABLE 3

| | Dosage of active compound g/ha | Herbicidal effect on weeds | | | | | | Phytotoxic effect on soybeans |
| | | Barnyard grass | Finger grass | Goose grass | Green foxtail | Causeway grass | Bermuda grass | |
|---|---|---|---|---|---|---|---|---|
| Active compound No. | | | | | | | | |
| 3 | 500 | 10 | 10 | 10 | 10 | 10 | 10 | 2 |
|  | 200 | 10 | 10 | 10 | 10 | 9 | 10 | 1 |
|  | 100 | 9 | 9 | 9 | 9 | 9 | 9 | 0 |
| 37 | 500 | 10 | 10 | 10 | 10 | 10 | 10 | 2 |
|  | 200 | 10 | 10 | 10 | 10 | 8 | 10 | 1 |
|  | 100 | 9 | 9 | 9 | 9 | 7 | 10 | 0 |
| 67 | 500 | 10 | 10 | 10 | 10 | 9 | 10 | 1 |
|  | 200 | 10 | 10 | 10 | 10 | 7 | 10 | 0 |
|  | 100 | 9 | 9 | 9 | 8 | 6 | 9 | 0 |
| 83 | 500 | 10 | 10 | 10 | 10 | 9 | 10 | 1 |
|  | 200 | 10 | 10 | 10 | 10 | 9 | 10 | 0 |
|  | 100 | 9 | 7 | 9 | 9 | 7 | 9 | 0 |
| 89 | 500 | 10 | 10 | 10 | 10 | 6 | 10 | 0 |
|  | 200 | 10 | 10 | 10 | 10 | 1 | 10 | 0 |
|  | 100 | 9 | 9 | 10 | 9 | 0 | 10 | 0 |
| 131 | 500 | 10 | 10 | 10 | 10 | 9 | 10 | 0 |
|  | 200 | 10 | 10 | 10 | 10 | 9 | 10 | 0 |
|  | 100 | 9 | 7 | 9 | 9 | 7 | 9 | 0 |
| 184 | 500 | 10 | 10 | 10 | 10 | 10 | 10 | 2 |
|  | 200 | 10 | 10 | 10 | 10 | 9 | 10 | 1 |
|  | 100 | 10 | 9 | 10 | 10 | 9 | 9 | 0 |
| Comparative | | | | | | | | |
| C-1 | 500 | 10 | 10 | 10 | 10 | 4 | 10 | 1 |
|  | 200 | 8 | 4 | 8 | 8 | 1 | 9 | 0 |
| C-2 | 500 | 10 | 10 | 9 | 7 | 2 | 10 | 0 |
|  | 200 | 9 | 7 | 5 | 4 | 0 | 8 | 0 |

It will be understood that the specification and examples are illustrative but not limitative of the present invention and that other embodiments within the spirit and scope of the invention will suggest themselves to those skilled in the art.

What is claimed is:

1. A 3-hydroxy-2-cyclohexen-1-one of the formula

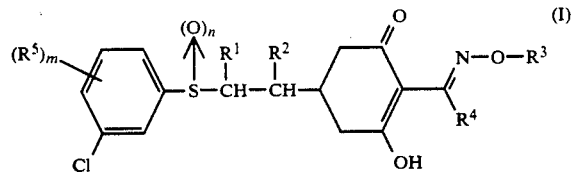

wherein

R$^1$ and R$^2$ each is hydrogen or methyl,
R$^3$ is C$_{1-4}$ alkyl, cyclopropylmethyl, C$_{3-4}$ alkenyl which may be substituted by one to three halogen atoms or C$_{3-4}$ alkynyl,
R$^4$ is C$_{1-4}$ alkyl,
R$^5$ each independently is halogen, C$_{1-4}$ alkyl, C$_{1-4}$ haloalkyl, C$_{1-4}$ alkoxy, C$_{1-4}$ haloalkoxy, C$_{1-4}$ alkylthio, C$_{1-4}$ haloalkylthio or cyano,
n is 0, 1 or 2, and
m is 0, 1 or 2.

2. A compound according to claim 1, wherein R$^1$ and R$^2$ each is hydrogen or methyl,
R$^3$ is C$_{1-4}$ alkyl or C$_{3-4}$ alkenyl which may be substituted by one to three halogen atoms,
R$^4$ is C$_{1-3}$ alkyl,
R$^5$ each independently is chlorine, fluorine or trifluoromethyl,
n is 0, 1 or 2, and
m is 0, 1 or 2.

3. A compound according to claim 1, wherein R$^1$ and R$^2$ each is hydrogen,
R$^3$ is ethyl or allyl,
R$^4$ is methyl or ethyl,
R$^5$ is chlorine, fluorine or trifluoromethyl,
n is 0, and
m is 0 or 1.

4. A compound according to claim 1, wherein such compound is 5-[2-(3,4-dichlorophenylthio)ethyl]-3-hydroxy-2-(1-ethoxyimino)propyl-2-cyclohexen-1-one of the formula

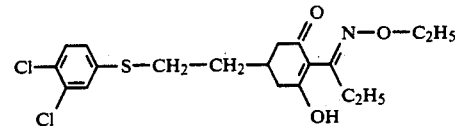

5. A compound according to claim 1, wherein such compound is 5-[2-(3-chlorophenylthio)ethyl]-3-hydroxy-2-(1-ethoxyimino)propyl-2-cyclohexen-1-one of the formula

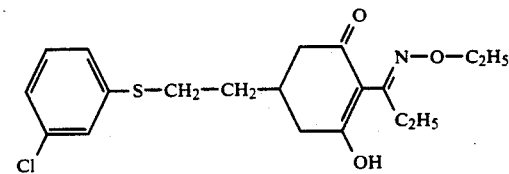

6. A compound according to claim 1, wherein such compoundis 5-[2-(3-chloro-4-fluorophenylthio-ethyl]-3-hydroxy-2-(1-ethoxyimino)propyl-2-cyclohexen-1-one of the formula

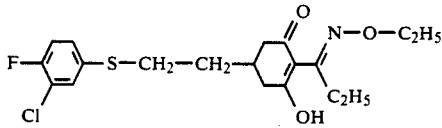

7. A compound according to claim 1, wherein such compound is 5-{2-[3-chloro-4-trifluoromethyl)-phenylthio]ethyl}-3-hydroxy-2-(1-ethoxyimino)ethyl-2-cyclohexen-1-one of the formula

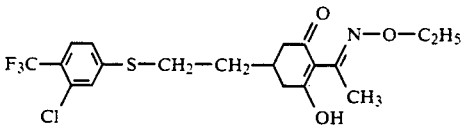

8. A compound according to claim 1, wherien such compound is 5-[2-(3-chloro-2-methylphenylthio)ethyl]-3-hydroxy-2-(1-allyloxyimino)propyl-2-cyclohexen-1-one of the formula

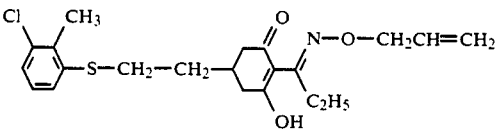

9. A compound according to claim 1, wherein such compound is 5-[2-(3-chloro-4-fluorophenylthio)ethyl]-3-hydroxy-2-(1-allyloxyimino)propyl-2-cyclohexen-1-one of the formula

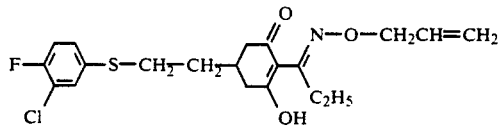

10. A compound according to claim 1, wherein such compound is 5-[2-(2-methyl-3-chloro-phenylthio)ethyl]-3-hydroxy-2-(1-ethoxyimino)propyl-2-cyclohexen-1-one of the formula

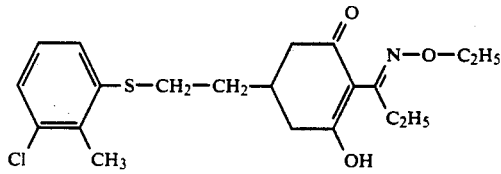

11. A herbicidal composition comprising a herbicidally effective amount of a compound according to claim 1 and a diluent.

12. A method of combating unwanted vegetation which comprises applying to such vegetation or to a locus from which it is desired to exclude such vegetation a herbicidally effective amount of a compound according to claim 1.

13. The method according to claim 12, wherein such compound is

5-[2-(3,4-dichlorophenylthio)ethyl]-3-hydroxy-2-(1-ethoxyimino)propyl-2-cyclohexen-1-one, 5-[2-(3-chlorophenylthio)ethyl]-3-hydroxy-2-(1-ethoxyimino)propyl-2-cyclohexen-1-one, 5-[2-(3-chloro-4-fluorophenylthio)ethyl]-3-hydroxy-2-(1-methoxyimino)propyl-2-cyclohexen-1-one, 5-{2-[3-chloro-4-(trifluoromethyl)-phenylthio]ethyl}-3-hydroxy-2-(1-ethoxyimino)ethyl-2-cyclohexen-1-one, 5-[2-(3-chloro-2-methylphenylthio)ethyl]-3-hydroxy-2-(1-allyloxyimino)propyl-2-cyclohexen-1-one, 5-[2-(3-chloro-4-fluorophenylthio)ethyl]-3-hydroxy-2-(1-allyloxyimino)propyl-2-cyclohexen-1-one or 5-{2-(2-methyl-3-chloro-phenylthio)ethyl}-3-hydroxy-2-(1-ethoxyimino)propyl-2-clclohexen-1-one.

* * * * *